US006344021B1

(12) United States Patent
Juster et al.

(10) Patent No.: US 6,344,021 B1
(45) Date of Patent: Feb. 5, 2002

(54) MAGNETIC THERAPY PATCH

(76) Inventors: Robert W. Juster, 6225 Reserve Cir. #1103, Naples, FL (US) 34119; James W. Carpenter, Jr., 815 Farwell Dr., Maple Bluff, WI (US) 53704

(*) Notice: Subject to any disclaimer, the term of this patent is extended or adjusted under 35 U.S.C. 154(b) by 0 days.

(21) Appl. No.: 09/518,201

(22) Filed: Mar. 3, 2000

(51) Int. Cl.[7] .................................................. A61N 1/00
(52) U.S. Cl. ............................................. 600/15; 600/9
(58) Field of Search ....................... 600/9, 15; 606/204; 604/180; 424/447

(56) References Cited

U.S. PATENT DOCUMENTS

| | | | | |
|---|---|---|---|---|
| 4,391,270 A | * | 7/1983 | Uragami | 600/15 |
| 4,798,194 A | * | 1/1989 | Amishima | 600/9 |
| 5,662,925 A | * | 9/1997 | Elbert et al. | 424/447 |
| 5,792,176 A | * | 8/1998 | Chang | 606/204 |
| 5,800,402 A | * | 9/1998 | Bierman | 604/180 |

\* cited by examiner

*Primary Examiner*—Eric F. Winakur
*Assistant Examiner*—Nikita Veniaminov

(57) ABSTRACT

The invention is concerned with magnetic therapy. To this end there are disclosed magnetic adhesive patches having at least one magnet thereon to be placed directly on the skin of a person. The adhesive patch has a hypoallergenic adhesive on one side on which side at least one magnet is placed thereon. The adhesive/magnetic combination has visual or tactile guides thereon for a correct placement of the any of the magnets relative to the adhesive patch. The adhesive patch, prior to a use, may be placed on a stiff retainer/release liner having one or more depressions therein to accommodate the one or more magnets that are attached to the adhesive side of the adhesive patch. There are disclosed replacement patches for the original patches that may have served a useful life. The replacement patches, on their adhesive side, have a peel-off backing that has a separation line off-set from a center of the adhesive patch which separation line is used as a guide for an edge of said one or more magnets to orient the magnets in a correct alignment on the replacement patch.

20 Claims, 7 Drawing Sheets

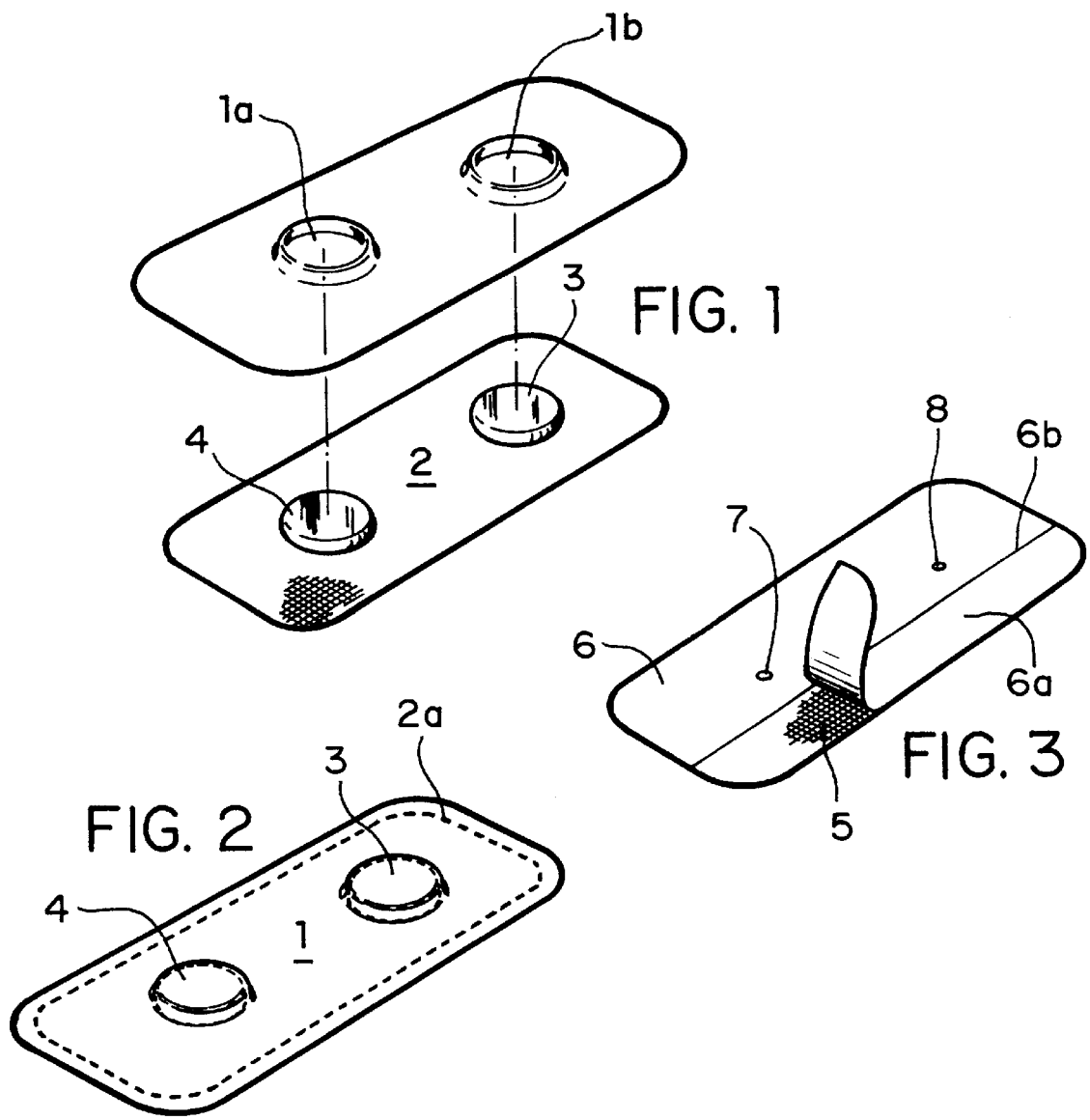

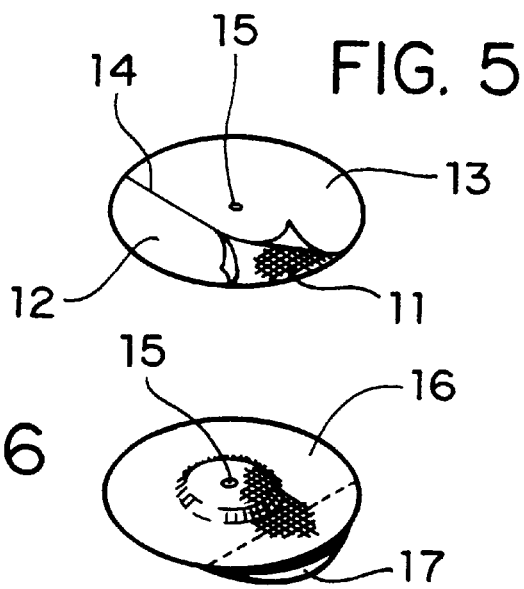
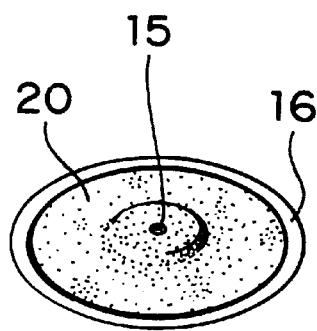
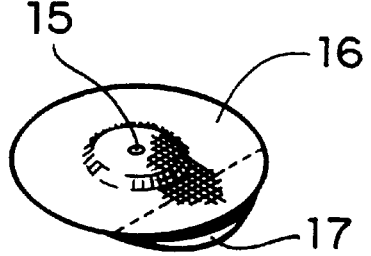
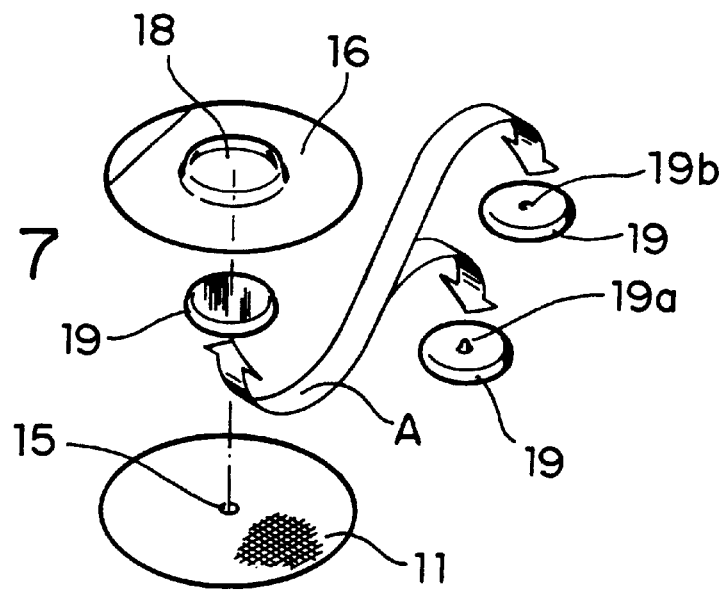

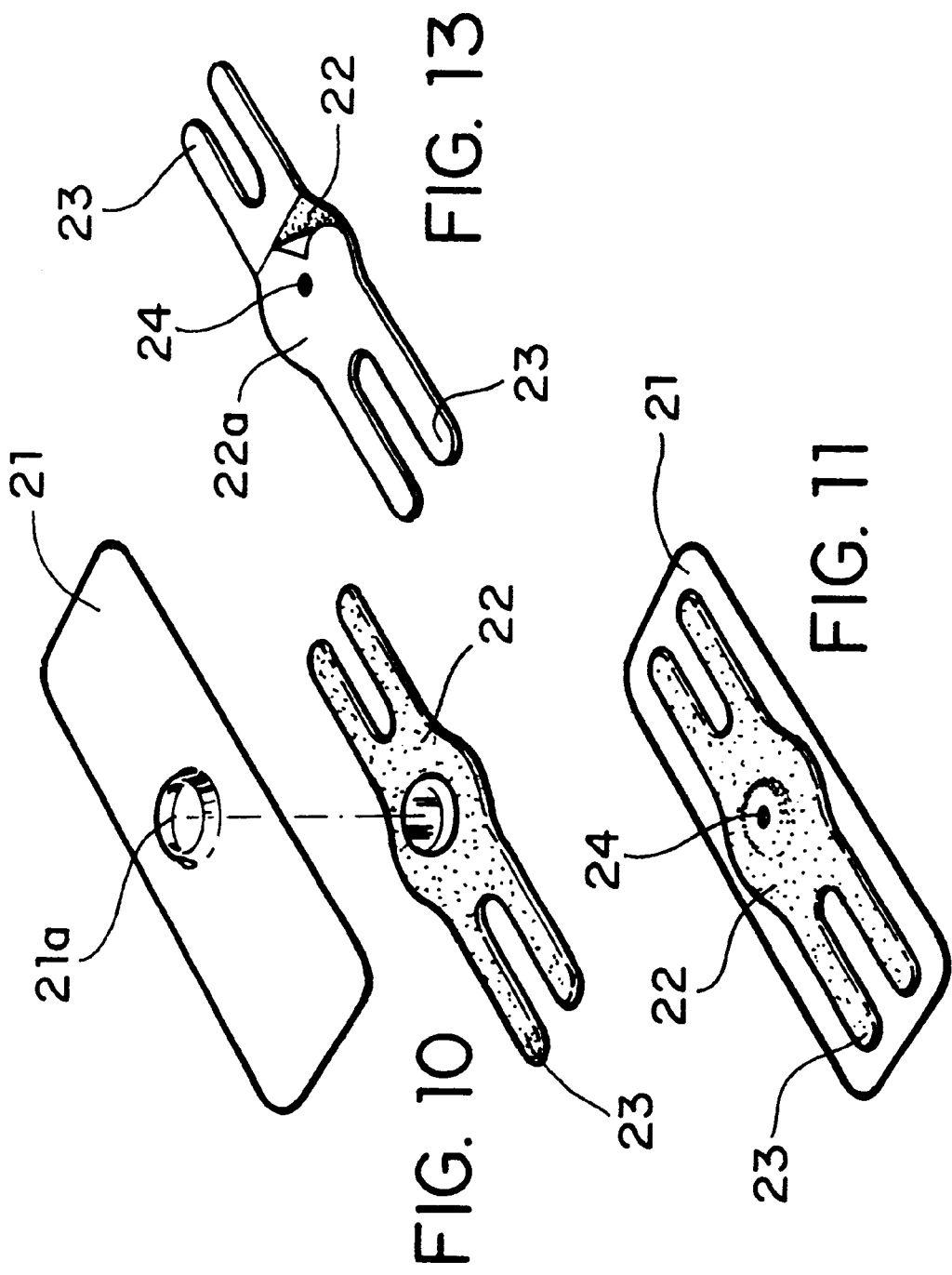

MAGNETIC THERAPY PATCH

BACKGROUND OF THE INVENTION

The invention pertains to a magnetic therapy patch which can instantly be applied to any part of the body where there is a need because of pain and other afflictions. In China, France, Japan and especially in India, magnetic therapy has long been used to speed the healing of broken bones and soft-tissues injuries. In the US, magnetic therapy is sometimes considered a form of quackery. But following the publication of several pro-magnet studies in the *Journal of Electro and magnetobiology* and other prestigious American medical journals, a few pioneering doctors in this country are starting to use magnets in their practices, Already, magnetic therapy has proven effective at treating slow healing fractures and arthritic knees and necks. Studies also suggest that regular use of magnets may reverse osteoporosis, prevent heart disease, slow tumor growth and boost mental function in Alzheimer's patients.

Is magnetic therapy safe? Absolutely. Magnetic Resonance Imaging (MRI) machines routinely expose patients to magnetic fields as high as 15,000 "gauss" with no negative effects. It stands to reason that a medical magnet rated at much less gauss poses little if not any threat at all.

Recent studies have demonstrated quite clearly that when placed directly on the skin, a simple hand-held magnet increases the flow of blood. It does so by stimulating cellular activity through the so-called "Hall effect".

Some scientists think magnets improve the functioning of the autonomic nervous system, which would also stimulate blood flow to the affected area. Magnetic therapy diminishes pain.

This occurs via a combination of the "Hall" effects and possibly some stabilizing influence on the autonomic nervous system. Magnetic therapy speeds healing by promoting a natural environment It does so by boosting the body's synthesis of adenosine triphosphate (ATP), the fuel that fires all cellular processes and by enhancing the blood's ability to carry oxygen. How does magnetic therapy work? Life is electrical in nature. Each individual cell posses a positive electrical charge at its nucleus and a negative electrical charge on its outer membrane. The functioning of the cells and the nervous system of every living being depends on direct current (DC) and pulsed DC energy. Without this energy, there is no life.

Magnetic therapy helps relieve arthritic pain and slows the deterioration of cartilage inside arthritic joints. It is recommended that patients with arthritis sleep on a magnetic mattress pad. The applicants' co-pending application Ser. No. 09/238,798 under the title of "Mattress cap with an expandable compartment" teaches the use of magnetic pads for just this purpose. This would also include magnetic pillow liners as an effective treatment for chronic headaches and jaw pain.

Tennis elbow, carpal tunnel syndrome and other tendon or ligament problems heal faster when wrapped in magnetic bandages. In most cases the magnet is wrapped into place over the effected area and left in place until the pain disappears.

In some hospitals, when dealing with broken bones, powerful electromagnets are being used to speed healing of stubborn bone fractures. Magnetic therapy also seems to promote regeneration of spinal disk tissue.

When dealing with asthma, the use of magnets helps prevent the violent allergic reaction in the lungs that is characteristic of bronchial asthma. Again it is recommended to sleep on a magnetic pad or the wearing of a magnetic bandage on the chest.

The benefits of magnetic therapy are often apparent within the first hour of treatment. With others, three or four days of steady treatment are required.

For maximum benefit, the magnets should be placed as close to the body as is possible. The strength of the magnetic field drops off sharply when the distance to the body increases. A variety of magnetic devices is now available including mattress pads, pillow liners, magnetic-studded bandages and simple hand-held magnets. A few of the prior art devices will now be discussed.

U.S. Pat. No. 3,943,912 relates to a medical treatment apparatus such as belly-band that is to be worn around the belly of a user. The belly-band includes magnetic treatment means that is attached thereto so that the belly-band can serve to protect the user's belly from being chilled and at the same time to magnetically treat any affected part of the body of the user's body.

U.S. Pat. No. 4,587,956 discloses a reversible magnetic therapeutic device including a two-sided flexible wrapper which includes a plurality of magnets sufficiently sized and spaced apart along the wrapper's length to provide a therapeutically effective two-dimensional array with all the north poles and all the south poles on opposite sides. The wrapper is wrapped in a sleeve form about an ailing body part. The wrapping seems to be quite complicated by having to observe the north and the south poles.

U.S. Pat. No. 5,312,321 discloses an octapolar magnetic device that is disposed near the mammalian sensory neuron so that the magnetic field generated by one quadrapolar face of the device is symmetrically disposed about the neuron. The magnetic device is comprised of four magnetic bodies, each having two opposite magnetic poles. Two positive and two negative poles are disposed substantially in a single plane to define the four vertices of a quadralateral shape, the two positive poles defining two diagonal vertices, and the two negative poles defining the opposite two diagonal vertices of the qudralateral shape. A housing is provided to hold the magnetic bodies in a fixed relative position and thus maintain the quadralateral orientation.

U.S. Pat. No. 5,707,333 discloses a method for preventing or reducing sensation originating in a part of the human body through the application of magnetic flux either to the lumbar-sacral region of the body or to the cervico-dorsal region of the body. The magnetic devices are supported on the human body in various locations as required and/or desired by a full range of comfort support products including back, shoulder, knee, foot ankle wrist, forearm and elbow.

There is a known publication by W. L. Roper, Chairman of Magnatherapy, Inc. under the title of "TECTONIC™ MAGNETS", The Invisible Massage That Lets You Feel The Difference". Tectonic magnets are unidirectional (unipolar) ceramic and flexible magnets that offer comfort for aches and pains. Each magnet is made to fit on a specific part of the body that has pain. Leading scientists agree that unipolar magnets are superior to bi-polar magnets. TECTONIC™ Power Magnets create magnetic fields which penetrate deeper into the target tissue, enhancing the flow of oxygen, ions and nutrients. The "gauss" rating of these magnetic devices range from a low of 1100, 2450, 3950 to 11000. They are applied to the body by special supporters or by surgical adhesive tapes.

Another publication is distributed as a brochure by *New Age Health Innovations* under the ™ of MAGNA POD Support System. The published magnetic devices involve the so-called Neodymium Magnets with alternating poles which consist of two layers indicated as a South pole and a North pole and are color coded to identify the same as to their polarity. The publication discloses that the MAGNA POD™ magnetic devices are applied to the body by a support system around various limbs of the body back and support systems. The magnets are used as alternating north and south poles on a plate-like support.

Still another publication by WONDER COMFORTS™ Int. discloses magnetic devices under the phrase "All magnets Are Not Created Equal". The magnetic devises used in this publication, under the name of BIOflex™, are applied to the body through the use of various support bandages or support sleeves. Other applications show the use of single round disks with the connotation "for placement use adhesive disks.

Still another publication by "Pjan International, Inc. in Stow, Ohio, discloses the use of a belt under the name "Magnetic Back/Belly Belt". In this belt, which can be worn on the back or the front of a user, there are embedded 16 large circular disc magnets and 54 tiny unique Pyramid points also embedded in the belt.

Attention is also directed to the publication distributed by the Magnet Sales & Manufacturing Co. Inc. of Culver City, Calif. Disclosed therein are all different kinds of magnets including the Neodymium Magnets. None of these magnets disclosed therein make any reference to the use of any magnetic devices to be worn on the body.

OBJECTS OF THE INVENTION

An object of the invention is to greatly simplify the use of magnets on the body for therapeutic purposes and at the same time to render them more effective. To this end, the magnets are directly worn on the skin of the body. In discussing the above noted various prior art devices the "gauss" rating of the magnets played a major role when the magnets were applied to the body. Experimentation has shown that, when magnets are worn by using supporters such as sleeves around body limbs or other devices around the neck and/or the shoulder, the effectiveness of the magnets contained therein is decreased through the intermediary presence of bandages or cloth because the "gauss" rating decreases the farther the magnet is removed from the affected areas such as muscles, blood vessels, joints or tissues. Therefore, the inventor is placing the magnets directly on the skin of the user. Various sizes of the magnets are contemplated such as round, square, rectangular or the use of multiple magnets where so desired or indicated. The problem is to fasten or adhere these magnets to the skin in a permanent manner. the skin of the body is prone to move and to flex. Another problem is the perspiration factor which almost defeats the adherence of anything that is placed on the skin. Some of the publications, described above, suggest the use of surgical tape which may be effective but the problem is that the magnets and the surgical tape may not be handy or available at the same time when needed. Another publication suggests the use of adhesive disks. The problem with this is that the disks cannot flex with the skin and are bound to loosen up after some use. According to the invention, adhesive bands or patches are being used that are well known in the area of disposable electrode assemblies in the testing of patients on treadmills. These pads or adhesive patches appear in a publication of a leading electrode Co. The patches or bandages use the natural adhesive Karaten, it inhibits skin irritations and promotes skin comfort. There is no skin preparation necessary for most patients and perspiration will not inhibit the magnet adhesion, while in fact, it enhances adhesive properties.

The magnet units of the invention are self-contained and are ready to use anywhere on the body of a user. The units include a relatively thin transparent base support member having a central depression for receiving the thickness of a magnet and to protect the same from handling prior to its use and to adhesively maintain the adhesive patch or bandage prior to its use. It is also extremely important to maintain the polarity of the magnets in their proper orientation when they are applied to the body. In this respect, the north pole, that is, the negative pole should always be in contact with the skin of the body. To this end, the magnets are all marked with their orientation so that the polarity can always be identified either by sight or by feel. It is also an object of the invention to assemble a kit of the various parts to be used in conjunction with the use of the magnets. It is believed that the adhesive patches or bandages are disposable after at least one use. The kit would contain extra patches or adhesive bandages, properly protected like a band-aid to be used in conjunction with the still usable magnets. The adhesive patches or bandages, however would also have an orientation aid, either visual or tactile, to match the proper orientation of the magnets with respect to their positive or negative poles.

BRIEF DESCRIPTION OF THE DRAWINGS

FIG. 1 is an exploded view of a magnetic patch and a retainer/release liner;

FIG. 2 shows an assembled magnetic patch with a retainer/release liner;

FIG. 3 illustrates a replacement patch for magnets;

FIG. 5 shows a replacement patch for a single magnet;

FIG. 6 is an illustration of a single magnet patch with a retainer/release liner;

FIG. 7 is an exploded view of a magnet non-woven patch and a retainer/release liner FIG. 8 illustrates an assembled magnetic foam vinyl/mylar patch with a retainer/release liner;

FIG. 10 shows an exploded view of a digital magnetic patch;

FIG. 11 illustrates an assembled magnetic digital patch;

FIG. 13 illustrates a replacement digital patch

DETAILED DESCRIPTION OF THE INVENTION

Figure 4:
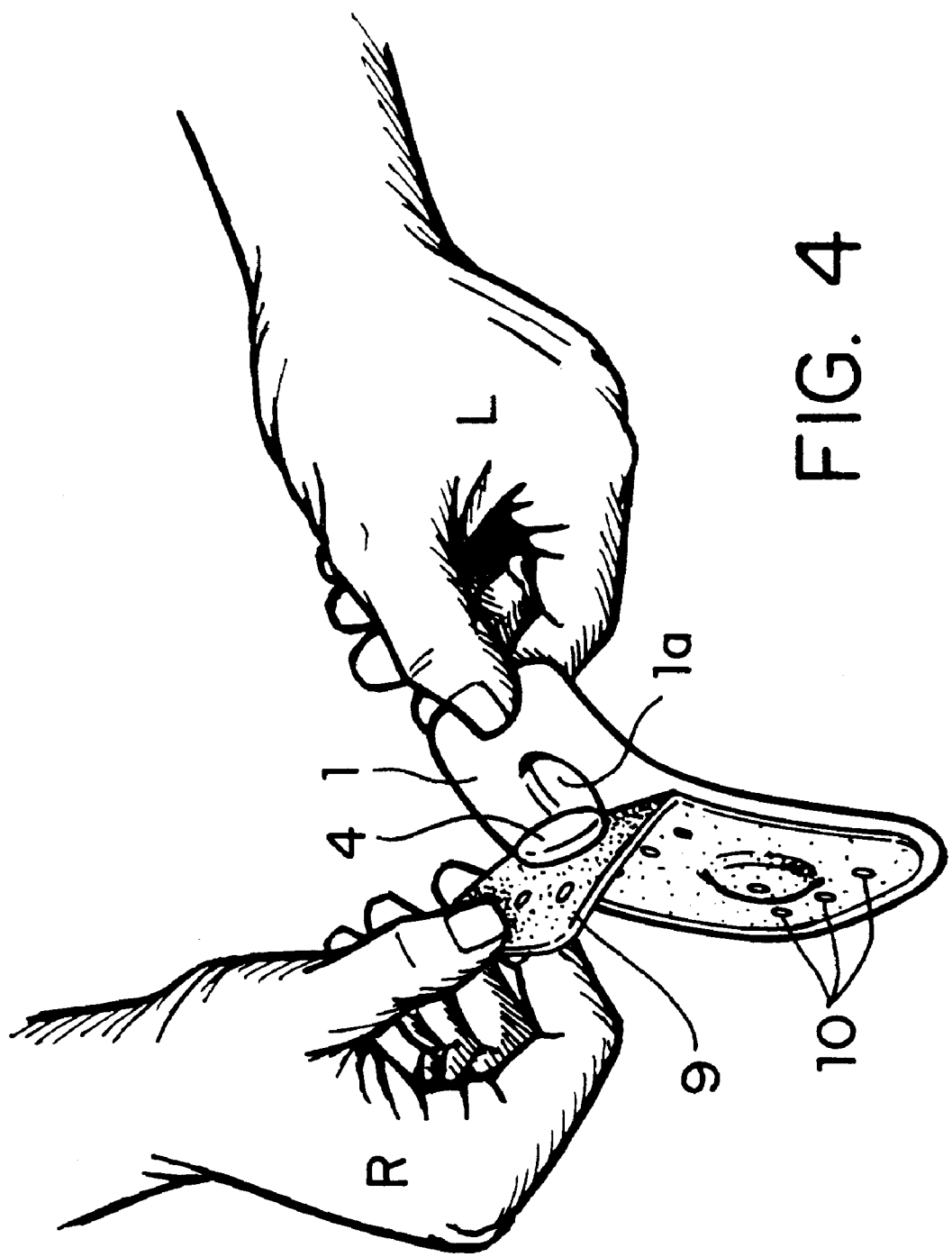
FIG. 4 shows a manner of peeling a patch away from a retainer/release liner.

FIG. 1 shows an exploded view of the magnetic patch in relation to a stiff retainer. The stiff retainer 1 illustrated in FIG. 1 is a thin piece of a plastic material made of either polystyrene or polyethylene and it can be either transparent or translucent. Impressed or molded into the stiff retainer is a first depression 1a and a second depression 1b which are designed to receive the first magnet 4 and a second magnet 4, respectively, on the adhesive patch 2 so that the magnets cannot be disturbed in any way and therefore will remain adhesively attached to the adhesive patch 2. It is contemplated that more than two magnets could be used on the same patch. Two or more magnets are considered to be multiples. The medical grade adhesive on the adhesive patch 2 is hypoallergenic and is designed to withstand active sports endeavors, including perspiration and frequent showering. The patch can be worn for several days without replacement. The adhesive patch can be a non-woven material of a polyester fabric which is coated with a skin contact pressure sensitive acrylic adhesive. As mentioned above, the adhesive backing is hypoallergenic.

FIG. 2 illustrates an assembled patch and retainer/release combination wherein like reference characters have been applied to the same elements. Thus, in FIG. 2 there is shown the stiff retainer at 1 and the outline of the adhesive patch 2 in the dashed outline as 2*a*. Again the numerals 3 and 4 show the depressions 3 and 4 in the stiff retainer 1. It is noted that the stiff retainer may be somewhat larger in its circumference than the adhesive patch 2. This will preserve the integrity of the adhesive patch 2 because nothing can encroach on the edges of the adhesive patch itself. This is the combination in FIG. 2 that a potential user of the magnetic patch will encounter at the point of sale.

Turning now to FIG. 3, there is shown a replacement adhesive patch 5 to be used as a replacement when the original adhesive patch 2 is deemed to be no longer serviceable because of continued use. The replacement adhesive patch 5 again can be a non-woven material of a medical grade quality and is backed with a two-sided poly coated lay flat release liner 6. The release liner is divided into two parts 6 and 6*a*, whereby 6*a* is divided from the liner 6 by a visible release line 6*b* which is used as an orientation line so that the magnets preserved from a previous use may be lined up at the line 6*a* so that the magnets 3 and 4 can be placed at a proper location. The numerals 7 and 8 are also designated as alignment holes to be explained below.

Turning now to FIG. 4, there is shown a manner or procedure of how to peel the backing or stiff retainer 1 away from the adhesive patch 9 having the magnets 3 and 4 thereon. The right hand R, as seen by looking from the person, grasps the adhesive patch 9 to peel it back while the left hand L grasps the stiff retainer 1 to pull it away from the adhesive patch 9. One of the magnets 4 is visible as it has been taken out of the depression 1*a* of the stiff retainer. The numeral 10 indicates ventilation holes in the adhesive patch 9. The adhesive patch in this case is depicted as a vinyl foam which through experimentation has been found to be more pliable in some applications. It is coated with a removable pressure sensitive acrylic adhesive on one side and skin contact pressure sensitive acrylic adhesive on the second side and it is backed with a two side silicone coated double face release liner. The pressure sensitive acrylic adhesive is a hypoallergenic adhesive and meets the USP class 6 standard and satisfies tripartite guidelines for skin contact devices. This adhesive does not contain any latex.

FIG. 5 shows a round replacement patch for a single magnet 19 which is shown in FIG. 7. This patch is being used for a replacement when the original patch can no longer being used. For this purpose, the replacement patch consists of the non-woven adhesive patch 11 which has two peel-off liners 12 and 13. The peel-off liner 13 is larger than the peel-off liner 12 and they are separated by an alignment line 14. The alignment line 14 is used so that the magnet 19 can be aligned in its correct position on the adhesive patch 11. This is achieved by simply aligning the edge of the magnet against the line 14. The numeral 15 indicates another alignment aid for the magnet 19. This feature will be described below with reference to FIG. 7.

FIG. 6 illustrates the fully assembled magnetic patch at the point of sale and shows how the adhesive patch can be peeled away at 17.

FIG. 7 is an exploded view of an adhesive patch 11 and a stiff retainer 16. In this view it shows the stiff retainer 16 with a depression 18 therein which receives the magnet 19 being adhesively attached to the adhesive patch which in turn is attached to the retainer until it is ready for use. This combination is found at the point of sale. A detailed explanation now follows with regard to the above mentioned other alignment feature for the magnet 19 relative to the adhesive patch 11. The hole 15 seen in FIGS. 5, 6, and 7 serve the purpose of aiding in aligning a previous used magnet with a new patch 11 because the previous magnetic patch has served its useful life but the magnet 19 can further be used. To this end, The magnets 19 have a tactile 19*a* or a visual 19*b* identifier to aid in aligning the magnets in their proper position on the adhesive patch 11. The tactile stipple 19*a* on the magnet 19 can be aligned with the adhesive patch 11 by feeling the stipple in the hole 15 of the adhesive patch. On the other hand, the depression 19*b* can be visually aligned with the hole 15 in the adhesive patch 11. The arrow A in FIG. 7 indicates the alternative uses of the alignment devices. Also the depression 18 in the stiff retainer 16 helps to preserve the integrity of the magnet 19 prior to use and while located at the point of sale.

FIG. 8 shows the magnetic adhesive patch 20 combined with the stiff retainer 16 at the point of sale. The shading in this FIG. 8 shows the use of a vinyl foam adhesive patch as was explained above with reference to FIG. 4. The advantages of using this type of adhesive patch have been explained above and will be further explained below.

Figure 9:
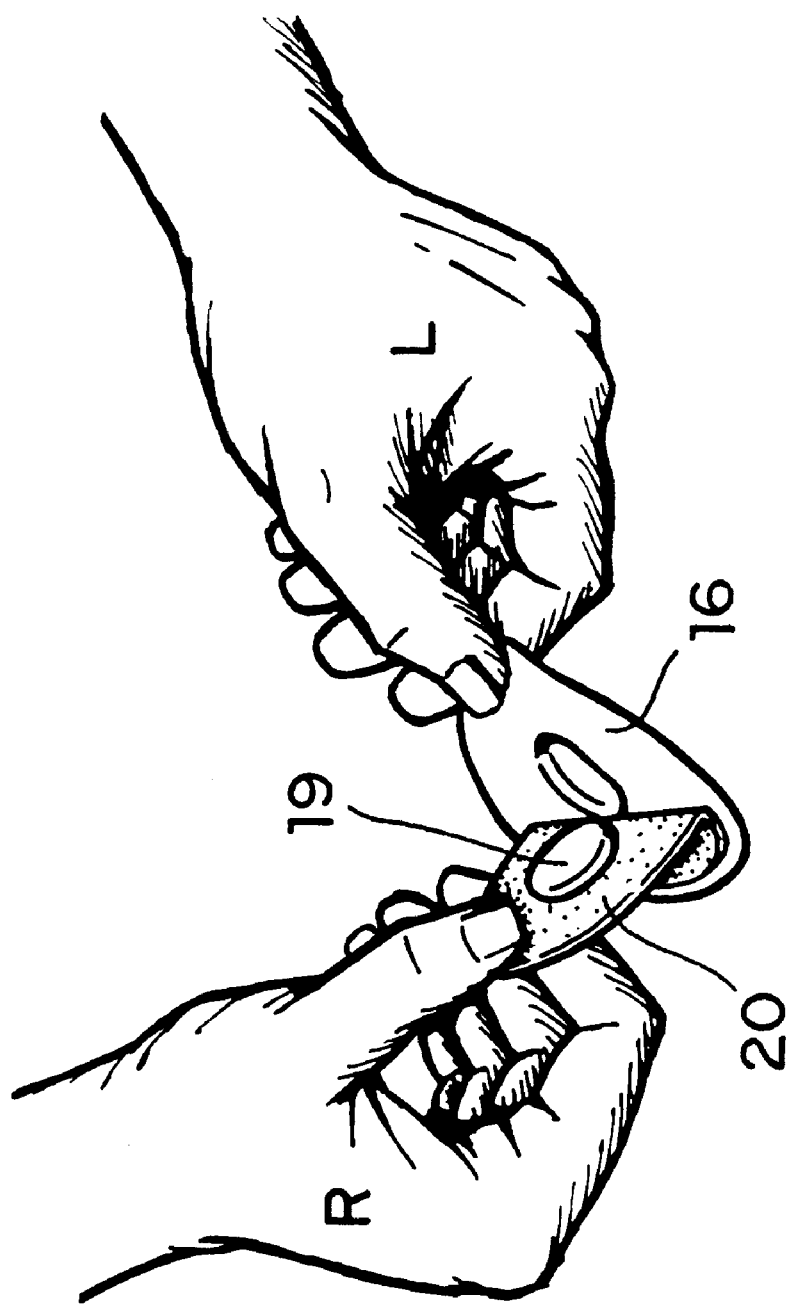
FIG. 9 shows a manner of peeling the assembled patch of FIG. 8.

FIG. 9 again shows the manner or procedure for peeling away the stiff retainer 16 from the vinyl foam patch 20 having the magnet 19 adhesively fastened thereon. The right hand R (as seen from the person) simply pulls the stiff retainer away from the adhesive patch 20 in the left hand L of the person. It should be noted that the retainer 16 again is somewhat larger than the adhesive magnet patch 20. As explained above, this is to keep the integrity of the edges of the magnetic adhesive patch intact prior to its use.

FIG. 10 is a view of still another therapeutic patch which is specially designed to be applied to fingers or the toes of a person. For this purpose, a vinyl foam adhesive patch 22 is highly desirable because it has some stretch and will effectively drape itself around the fingers of a person. Again at a point of sale, the patch 22 is adhered to the stiff retainer 21 which has the depression 21*a* to receive the magnet 19 therein to protect the same from the environment prior to its use. The patch 22 itself is subdivided into narrow extensions 23 having an elongated slot therebetween to aid in the adhesion of the patch 22 when being draped around a finger or a toe of a person making use of the therapeutic patch 22. The finger-like extensions 23 do not have to separated at their ends but could instead by bridged by a narrow connection.

FIG. 11 shows the same patch 22 as it is assembled on the stiff retainer 21. Again, the stiff retainer 21 may be somewhat larger than the adhesive patch 22 to keep the integrity of the edges of the patch 22 intact, shown at 24 is the orientation hole which aids in a proper alignment of the magnet 19 should the need arise.

Figure 12:
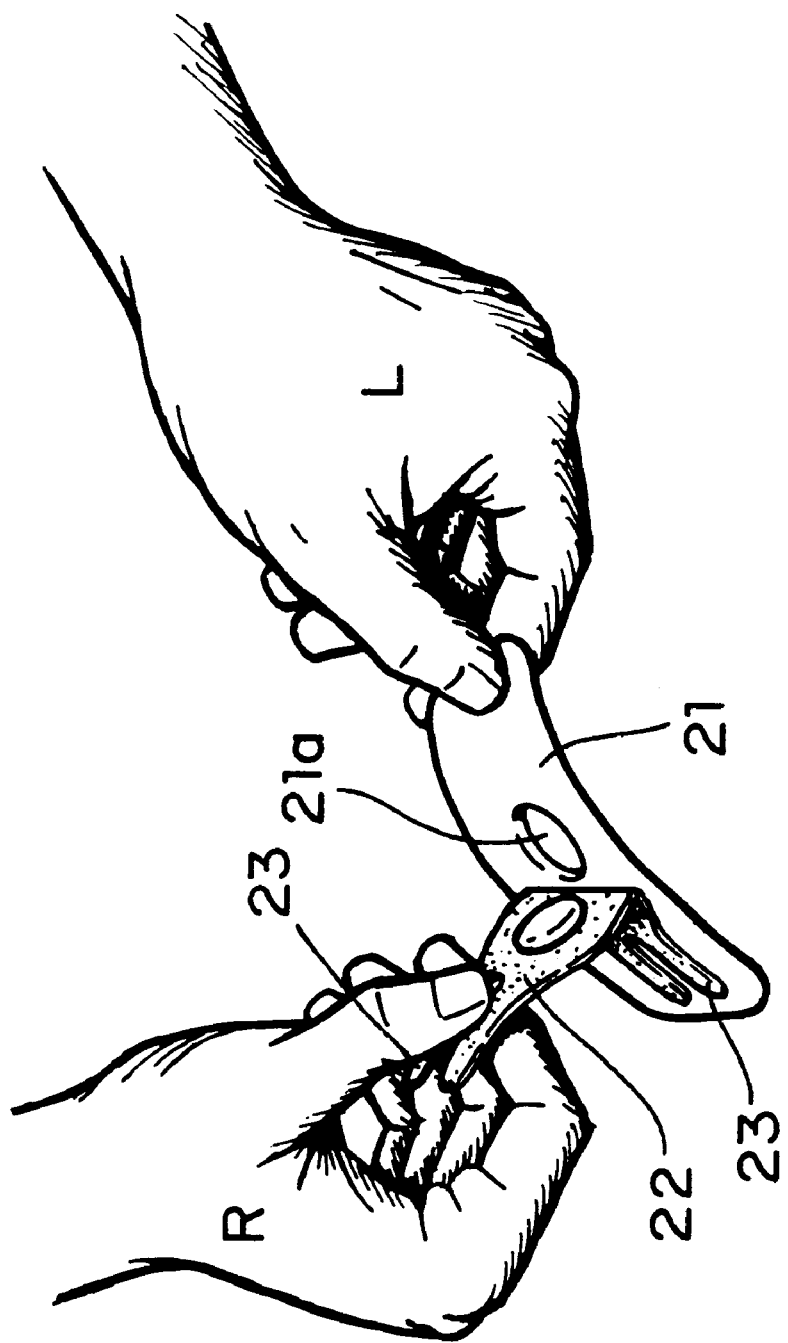
FIG. 12 shows the manner of peeling the assembled patch of FIG. 11.

FIG. 12 illustrates the manner or the proceeding by which the adhesive patch 22 is being separated from the stiff retainer 21. The right hand R (as seen from the person) grasps the adhesive patch 22 while the left hand L grasps the stiff retainer to be pulled away from the patch 22. Also, the depression 21a, that receives the magnet 19, can be seen and the finger-like extensions 23. A right-handed person would have the adhesive patch 22 correctly oriented to be applied to a chosen finger. Of course, a left-handed person would reverse the above noted procedure.

FIG. 13 illustrates a replacement adhesive patch 22 which again is made of a vinyl or mylar foam material. In this case, the vinyl foam material is adhesively attached to the removable liner 22a which again has a divider line against which the magnet 19 can be placed so as to be in its correct position. Also, the orientation hole 24 is used to either visually or by way of tactility align the magnet so that the correct polarity of the magnet can be observed. This was discussed supra in the description of FIG. 7, where it was disclosed that the magnet 19 has either a stipple 19a or a dimple 19b. With reference to FIG. 13 it is again noted that the replacement patch 22 is used when the original patch 22 (FIGS. 10 and 11) has served its useful life. In the original patch and retainer combination of FIGS. 10 and 11, the magnet 19 was already correctly aligned or placed on the adhesive patch at the point of sale. However, when a user uses a replacement patch 22 of FIG. 13, the magnet has to be correctly applied to the replacement patch 22 by the user, hence the alignment aids such as a liner divider line or the orientation hole 24.

Figure 14:
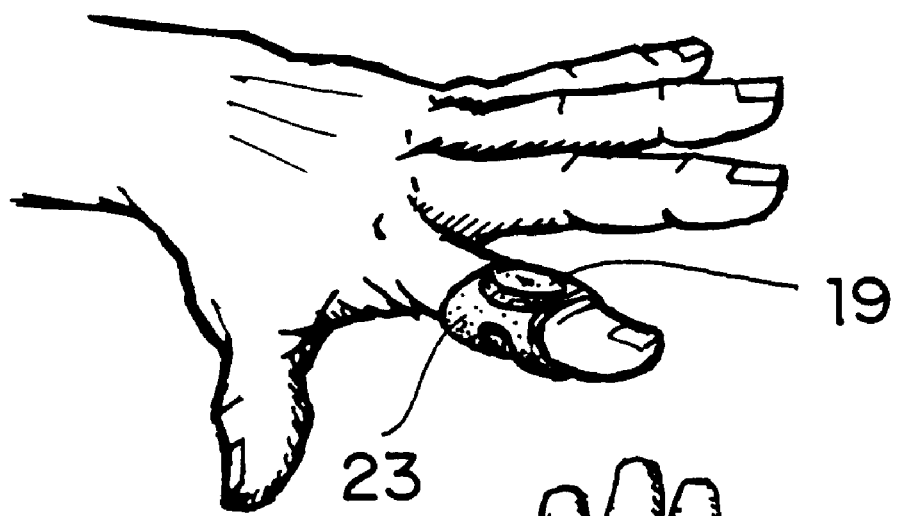
FIG. 14 shows a patch of FIGS. 10 and 11 as it is applied to a finger.
Figure 15:
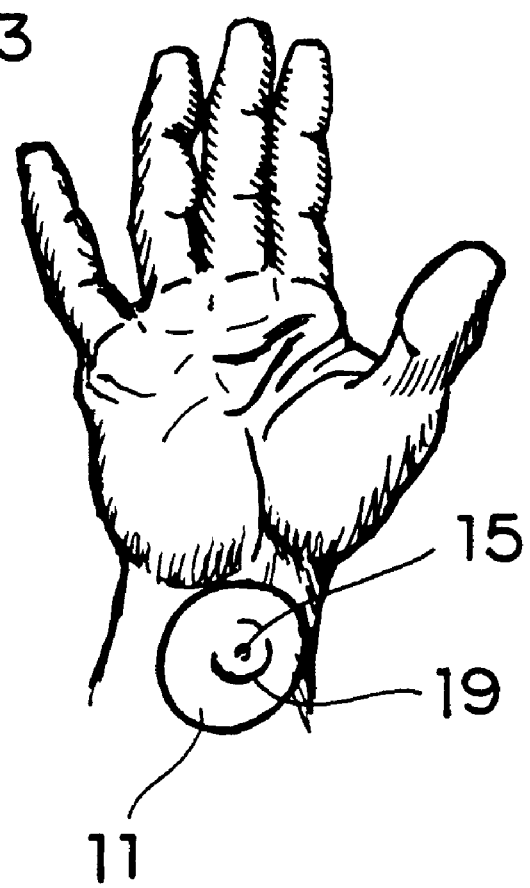
FIG. 15 shows a patch of FIGS. 6 and 7 as it is applied to a hand.

Turning now to FIG. 14, there is shown the therapeutic patch of FIGS. 10 and 11 as it is applied to a finger of a user.

FIG. 14 shows the therapeutic patch of FIGS. 6 and 7 as it is applied to a wrist of a user. Notice the adhesive patch 11 as seen from the outside, the hidden magnet 19 and the orientation hole 15.

Catalog of Reference Character

1 . . . stiff retainer/release liner
1a . . . first depression in stiff retainer 1
1b . . . second depression in stiff retainer 1
2 . . . adhesive patch
3 . . . first magnet on patch 2
4 . . . second magnet on patch 2
5 . . . replacement patch for magnets 3 and 4
6 . . . release liner
6a . . . part of release liner 6
6b . . . other part of release liner 6
7 . . . first alignment hole on patch 5
8 . . . second alignment hole on patch 5
9 . . . vinyl/mylar foam patch
10 . . . ventilation holes
11 . . . round non-woven replacement patch
12 . . . peel-off backing (small)
13 . . . peel-off backing (large)
14 . . . alignment line for magnet 19
15 . . . alignment hole for magnet 19
16 . . . round stiff retainer
17 . . . peel-off tab
18 . . . depression in stiff round retainer
19 . . . magnet
19a . . . tactile stipple on magnet 19
19b . . . visual dimple on magnet 19
20 . . . vinyl foam round adhesive patch catalog of reference characters (continued)

21 . . . oblong stiff retainer
21a . . . depression in stiff retainer 21 for receiving magnet 19
22 . . . vinyl foam adhesive patch for human digits
22a . . . release liner for replacement patch 22
23 . . . finger-like narrow extensions of patch 22
24 . . . alignment or orientation hole for magnet

What we claim is:

1. A therapeutic magnetic patch comprising an adhesive patch having a hypoallergenic adhesive placed thereon and adapted to be in contact with the skin of a user, a magnet in combination with said adhesive patch is placed on said patch and is also adapted to be in contact with the skin of the user, said adhesive patch having orientation means on an upper surface of said adhesive patch and magnet combination for assuring a correct orientation of the polarity of said magnet relative to the skin of the user.

2. The therapeutic magnet patch of claim 1, wherein said means for assuring a correct orientation is a visual orientation.

3. The therapeutic magnet patch of claim 1, wherein said means for assuring a correct orientation is a tactile orientation.

4. The therapeutic magnetic patch of claim 1, wherein said adhesive patch is a non-woven polyester fabric coated with a skin contact pressure sensitive acrylic adhesive and backed with a two side poly coated lay flat release liner.

5. The therapeutic magnetic patch of claim 1, wherein said adhesive patch is a top coated polyethylene foam coated with a removable pressure sensitive acrylic adhesive on one side and backed with a two side silicone coated double face release liner.

6. The therapeutic magnetic patch of claim 1, wherein said adhesive patch has a round shape.

7. The therapeutic magnetic patch of claim 1, wherein said adhesive patch has an oblong shape and multiple magnets placed thereon.

8. The therapeutic magnetic patch of claim 1, wherein said adhesive patch has ventilation holes placed therein.

9. The therapeutic magnetic patch of claim 1, wherein said adhesive patch has finger-like extensions placed thereon separated by an elongated slot.

10. A therapeutic magnetic patch comprising an adhesive patch having on one side thereof a hypoallergenic adhesive placed thereon, a magnet adhesively placed on said side having said hypoallergenic adhesive thereon, said adhesive side being placed on a stiff retainer, said stiff retainer being a means for retaining said patch until use, said stiff retainer having a depression therein to receive said magnet therein for storage, said stiff retainer being considerably stiffer than said adhesive patch.

11. The therapeutic magnetic patch of claim 10, wherein said stiff retainer has a circumference which is larger than the circumference of said adhesive patch.

12. The therapeutic magnetic patch of claim 10, wherein the adhesive patch and stiff retainer combination has an oblong shape having two separate magnets adhesively placed on said adhesive patch and said stiff retainer having two depressions formed therein to each receive a corresponding magnet of said adhesive patch.

13. The therapeutic magnetic patch of claim 10, wherein said adhesive patch has finger-like extensions thereon.

14. A therapeutic magnetic replacement patch comprising an adhesive patch having a hypoallergenic adhesive on one side thereof, said adhesive patch has a peel-off backing thereon, said backing is divided in two parts by a line of separation, said line of separation is off-set from a center line of said adhesive patch, a magnet placed on said adhesive side of said adhesive patch, said line of separation is an orientation guide for an edge of said magnet in order to place said magnet in a correct position on said adhesive patch.

15. The therapeutic magnetic replacement patch of claim 14, wherein said adhesive patch has a round shape.

16. The therapeutic magnetic replacement patch of claim 14, wherein said adhesive patch has an oblong shape having multiple magnets placed on said adhesive side.

17. The therapeutic magnetic replacement patch of claim 14, wherein said adhesive patch has finger-like extensions thereon separated by an elongated slot.

18. The therapeutic magnetic replacement patch of claim 14, wherein said adhesive patch has an orientation hole therein for a correct placement of said magnet.

19. The therapeutic magnetic replacement patch of claim 14, wherein said magnet has means thereon for a visual and tactile orientation relative to said adhesive patch.

20. The therapeutic magnetic patch of claim 14, wherein said adhesive patch has ventilation holes therein.

* * * * *